US008389689B2

(12) United States Patent
O'Neil et al.

(10) Patent No.: US 8,389,689 B2
(45) Date of Patent: Mar. 5, 2013

(54) ANTI-GLP-1R ANTIBODIES AND THEIR USES

(75) Inventors: Karyn O'Neil, Radnor, PA (US); Kristen Picha, Radnor, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 12/913,406

(22) Filed: Oct. 27, 2010

(65) Prior Publication Data

US 2011/0098443 A1  Apr. 28, 2011

Related U.S. Application Data

(60) Provisional application No. 61/255,532, filed on Oct. 28, 2009, provisional application No. 61/313,289, filed on Mar. 12, 2010.

(51) Int. Cl.
 C07K 16/28 (2006.01)
 A61K 39/395 (2006.01)
(52) U.S. Cl. .................. 530/387.1; 424/130.1
(58) Field of Classification Search ........... None
See application file for complete search history.

(56) References Cited

U.S. PATENT DOCUMENTS

| | | | |
|---|---|---|---|
| 6,818,749 | B1 | 11/2004 | Kashmiri et al. |
| 7,250,165 | B2 | 7/2007 | Heavner et al. |
| 2003/0032782 | A1 | 2/2003 | Nagy et al. |
| 2003/0054407 | A1 | 3/2003 | Luo |
| 2004/0170626 | A1 | 9/2004 | Schuurman et al. |
| 2006/0275288 | A1 | 12/2006 | Grihalde et al. |
| 2009/0137002 | A1 | 5/2009 | Petrul et al. |
| 2009/0175791 | A1 | 7/2009 | Kavile et al. |
| 2009/0191205 | A1 | 7/2009 | Gurney |

FOREIGN PATENT DOCUMENTS

| | | |
|---|---|---|
| WO | WO 2006/116155 A2 | 11/2006 |
| WO | WO 2007/070538 A9 | 6/2007 |
| WO | WO 2008/072723 A1 | 6/2008 |

OTHER PUBLICATIONS

Paul, William, Fundamental Immunology, 3rd Edition, Raven Press, New York, 1993, pp. 292-295.*
Vajdos et al., Comprehensive functional maps of the antigen-binding site of an anti-ErbB2 antibody obtained with shotgun scanning mutagenesis. J. Mol. Biol. 320:415-428, 2002.*
Aalberse, et al., IgG4 breaking the rules, Immunology, 105: 9-19 (2002).
Bullock, et al., Tissue Distribution of Messenger Ribonucleic Acid Encoding the Rat-Glucagon-Like Peptide-1 Receptor, Endocrinology, 137: 2968-2978 (1996).
Deckert, et al., "Pharmacokinetics and Microdistribution of Polyethylene Glycol-Modified Humanized A33 Antibody Targeting Colon Cancer Xenografts," International Journal of Cancer, 87: 382-390 (2000).

Drucker, et al., "Glucagon-Like Peptides: Regulators of Cell Proliferation, Differentiation, and Apoptosis," Molecular Endocrinology, 17: 161-171 (2003).
Drucker, et al., "Glucagon-like peptide I stimulates insulin gene expression and increases cyclic AMP levels in a rat islet cell line," Proceedings of the National Academy of Science USA, 84: 3434-3438 (1987).
Farilla, et al., "Glucagon-Like Peptide-1 Promotes Islet Cell Growth and Inhibits Apoptosis in Zucker Diabetic Rates," Endocrinology, 143(11): 4397-4408 (2002).
Huang, et al., "Discovery of human antibodies against the C5aR target using phage display technology," Journal of Molecular Recognition, 18: 327-333 (2005).
Hui, et al., "Glucagon-Like Peptide-1 Inhibits Apoptosis of Insulin-Secreting Cells via a Cyclic 5'-Adenosine Monophosphate-Dependent Protein Kinase A- and a Phosphatidylinositol 3-Kinase-Dependent Pathway," Endocrinology, 144: 1444-1455 (2003).
Knight, et al., "Pharmacodynamic enhancement of the anti-platelet antibody Fab abciximab by site-specific pegylation," Platelets, 15(7): 409-418 (2004).
Leong, et al., "Adapting Pharmacokinetic Properties of a Humanized Anti-Interleukin-8 Antibody for Therapeutic Applications Using Site-Specific Pegylation," Cytokine, 16 (13): 106-119 (2001).
Michel, et al., "How reliable are G-protein-coupled receptor antibodies?" Naunyn-Schmied Arch Pharmacology, 379: 385-388 (2009).
Mojsov, et al., "Preproglucagon Gene Expression in Pancreas and Intestine Diversifies at the Level of Pros-translational Processing," The Journal of Biological Chemistry, 261(25): 11880-11889 (1986).
David E. Moller, "New drug targets for type 2 diabetes and the metabolic syndrome," Nature, 414: 821-827 (2001).
Narayan, et al., "Diabetes—a common, growing, serious, costly, and potentially preventable public health problem," Diabetes Research and Clinical Practice, 50(Suppl. 2): S77-S94 (2000).
Orskov, et al., "Tissue and Plasma Concentrations of Amidated and Glycine-Extended Glucagon-Like Peptide I in Humans," Diabetes, 43: 535-539 (1994).
Perfetti, et al., "Glucagon-Like Peptide-1 Induces Cell Proliferation and Pancreatic-Duodenum Homeobox-1 Expression and Increases Endocrine Cell Mass in the Pancreas of Old, Glucose-Intolerant Rats," Endocrinology, 141: 4600-4605 (2000).
Sangawa, et al., "A Murine Monoclonal Antibody That Binds N-Terminal Extracellular Segment of Human Protease-Activated Receptor-4," Hybridoma, 27(5): 331-335 (2008).
Suzuki, et al., "Comparison of the Effects of Various C-Terminal and N-Terminal Fragment Peptides of Glucagon-Like Peptide-1 on Insulin and Glucagon Release from the Isolated Perfused Rat Pancreas," Endocrinology, 125(6): 3109-3114 (1989).
Valverde, et al., "Bioactive GLP-1 in Gut, Receptor Expression in Pancreas, and Insulin Response to GLP-1 in Diabetes-Prone Rats," Endocrine, 23(1): 77-84 (2004).
Wettergren, et al., "Truncated GLP-1 (Proglucagon 78-107-Amide) Inhibits Gastric and Pancreatic Functions in Man," Digestive Diseases and Sciences, 38(4): 665-673 (1993).
Wilmen, et al., "The isolated N-terminal extracellular domain of the glucagon-like peptide-1 (GLP)-1 receptor has intrinsic binding activity," FEBS Letters 398: 43-47 (1996).
Yang, et al., "Tailoring structure-function and pharmacokinetic properties of single-chain Fv proteins by site-specific PEGylation," Protein Engineering, 16(10): 761-770 (2003).
GenBank Accession No. Q070E2 (Retrieved from the Internet Apr. 17, 2011).
PCT International Search Report dated Oct. 31, 2011.

* cited by examiner

*Primary Examiner* — Ruixiang Li
(74) *Attorney, Agent, or Firm* — Kirk Baumiester (57) ABSTRACT

The present invention relates to antibodies reactive with GLP-1R, and methods of making and using them.

7 Claims, 2 Drawing Sheets

ANTI-GLP-1R ANTIBODIES AND THEIR USES

This application claims the benefit of U.S. Provisional Application No. 61/255,532, filed 28 Oct. 2009, and U.S. Provisional Application No. 61/313,289, filed 12 Mar. 2010, the entire contents of which are incorporated herein by reference.

FIELD OF THE INVENTION

The present invention relates to antibodies reactive with GLP-1R, and methods of making and using them.

BACKGROUND OF THE INVENTION

Diabetes is a growing epidemic that is estimated to affect over 300 million people by the year 2025, for which Type 2 diabetes accounts for 90-95% of all cases. Complications resulting from sustained elevated plasma glucose levels include cardiovascular disease, nephropathy, neuropathy, and retinopathy. In addition, the β-cells of the pancreas are destroyed and thus insulin secretion ceases during the later stages of the disease. Current treatments for diabetes can result in hypoglycemia and weight gain, and because patients may become resistant to treatment regimens over time, this may culminate in the need for insulin therapy at later stages of the disease (Narayan et al., Diabetes Research and Clinical Practice 50:S77-S84, 2000; Moller, Nature 414:821-827, 2001).

Glucagon like peptide-1 (GLP-1) is a 30-amino acid peptide (SEQ ID NO: 17) secreted from the L-cells of the intestine following an oral glucose challenge (Mojsov et al., J. Biol. Chem. 261:11880-11884, 1986; Orskov et al., Diabetes 43:535-539, 1994; Drucker et al., Proc. Natl. Acad. Sci. USA 84:3431-3438, 1987; Suzuki et al., Endocrinology 125:3109-3114, 1989). In response to glucose, GLP-1 binds to the GLP-1 receptor (GLP-1R) on the pancreas and induces insulin secretion (human GLP-1R amino acid sequence shown in SEQ ID NO: 1, mouse GLP-1R amino acid sequence shown in SEQ ID NO: 2). It has also been shown that GLP-1 reduces gastric emptying which decreases the bolus of glucose that is released into the circulation and may reduce food intake (Wettergren et al., Dig. Dis. Sci. 38:665-673, 1993). GLP-1 has also been shown to inhibit apoptosis and increase proliferation of the β-cells in the pancreas (Drucker et al., Mol. Endocrinology. 17:161-171, 2003; Perfetti et al., Endocrinology 141:4600-4605, 2000; Hui et al., Endocrinology 144:1444-1455, 2003; Farilla et al., Endocrinology 143:4397-4408, 2002). Thus, GLP-1 has attractive properties for a therapeutic to lower blood glucose and preserve the β-cells of the pancreas of diabetic patients.

It is likely that functional GLP-1 receptors localized in different types of tissues and cells contribute to the overall observed efficacy of the pleiotropic GLP-1 peptide. For example, it is unclear whether GLP-1 regulates food intake via a centrally or peripherally-mediated mechanism. Current GLP-1R tissue distribution studies have relied almost entirely upon mRNA levels rather than protein levels (Bullock et al., Endocrinology 137:2968-2978; Valverde et al., Endocrine 23:77-84, 2004). Further receptor biodistribution studies would benefit from the availability of specific GLP-1R antibodies that cross-react across species, thus facilitating measurement of protein levels for example in defined brain regions and peripheral tissues across multiple species. Antibodies that identify and neutralize the activity of the GLP-1R would facilitate phamacodynamic studies. For example, the antibody could be used as a tool to dissect the contributions of brain versus peripheral GLP-1 receptors that may be responsible for mediating GLP-1 effects.

Therefore, there is a need for antibodies against GLP-1R that facilitate biodistribution, pharmacodynamic, and mechanism of action studies of the GLP-1R and its ligands.

SUMMARY OF THE INVENTION

One aspect of the invention is an isolated antibody reactive with glucagon-like peptide receptor 1 (GLP-1R) comprising the amino acid sequences of the light chain complementarity determining regions (CDRs) 1, 2 and 3 as shown in SEQ ID NOs: 3, 4 and 5, respectively and the amino acid sequences of the heavy chain CDRs 1, 2 and 3 as shown in SEQ ID NOs: 6, 7 and 8, respectively.

Another aspect of the invention is an isolated antibody reactive with glucagon-like peptide receptor 1 (GLP-1R) comprising a light chain variable region (VL) having the amino acid sequence shown in SEQ ID NO: 9 and a heavy chain variable region (VH) having the amino acid sequence shown in SEQ ID NO: 10.

Another aspect of the invention is an isolated polynucleotide encoding an antibody light chain comprising the CDR amino acid sequences shown in SEQ ID NOs: 3, 4 and 5.

Another aspect of the invention is an isolated polynucleotide encoding an antibody heavy chain comprising the CDR amino acid sequences shown in SEQ ID NOs: 6, 7 and 8.

Another aspect of the invention is an isolated polynucleotide encoding an antibody light chain comprising the amino acid sequence shown in SEQ ID NOs: 9, 11 and 12.

Another aspect of the invention is an isolated polynucleotide encoding an antibody heavy chain comprising the amino acid sequence shown in SEQ ID NOs: 10, 13 and 14.

Another aspect of the invention is an isolated polynucleotide comprising a polynucleotide having a sequence shown in SEQ ID NOs: 15 and 16.

Another aspect of the invention is an isolated antibody light chain comprising the amino acid sequence shown in SEQ ID NOS: 9, 11 and 12.

Another aspect of the invention is an isolated antibody heavy chain comprising the CDR amino acid sequences shown in SEQ ID NOs: 10, 13 and 14.

Another aspect of the invention is a vector encoding the antibody heavy and light chains of the invention.

Another aspect of the invention is a host cell capable of expressing the isolated antibodies of the invention.

Another aspect of the invention is a method of making an antibody reactive with GLP-1R.

Another aspect of the invention is a hybridoma cell line expressing the isolated antibodies of the invention.

Table 1 shows the description of the sequence listing.

| SEQ ID NO: | Description |
|---|---|
| 1 | human GLP-1R |
| 2 | mouse GLP-1R |
| 3 | PHD 191 LC-CDR1 |

-continued

| SEQ ID NO: | Description |
|---|---|
| 4 | PHD 191 LC-CDR2 |
| 5 | PHD 191 LC-CDR3 |
| 6 | PHD 191 HC-CDR1 |
| 7 | PHD 191 HC-CDR2 |
| 8 | PHD 191 HC-CDR3 |
| 9 | PHD 191 LV |
| 10 | PHD191 HV |
| 11 | PHD 191 LC, human κ |
| 12 | PHD 191 LC, mouse κ |
| 13 | PHD 191 HC, human IgG1 |
| 14 | PHD 191 HC, mouse IgG2a |
| 15 | DNA, PHD 191 LC, human κ |
| 16 | DNA, PHD 191 HC, human IgG1 |
| 17 | GLP-1 (3-37) |

DETAILED DESCRIPTION OF THE INVENTION

All publications, including but not limited to patents and patent applications, cited in this specification are herein incorporated by reference as though fully set forth.

The term "antagonist" as used herein means a molecule that partially or completely inhibits, by any mechanism, an effect of another molecule such as a receptor or a ligand. An antagonist is capable of, directly or indirectly, substantially counteracting, reducing or inhibiting GLP-1R biological activity. Antagonists can be antibodies, proteins, peptides, or the like. For example, an antibody antagonist can bind directly to GLP-1R and inhibit GLP-1R biological activity.

The term "reactive with" refers to antibody binding to a predetermined antigen with greater affinity than it has for other antigens or proteins. Typically, a reactive antibody binds with a dissociation constant ($K_D$) of $10^{-7}$ M or less, and binds to the predetermined antigen with a $K_D$ that is at least tenfold less than its $K_D$ for a non-specific antigen (e.g., BSA, casein, or any other specified polypeptide). The phrases "an antibody recognizing an antigen" and "an antibody specific for an antigen" are used interchangeably herein with the term "an antibody reactive with an antigen" e.g., an antibody reactive with GLP-1R. The dissociation constant can be measured using standard procedures as described below.

The term "antibodies" as used herein is meant in a broad sense and includes immunoglobulin or antibody molecules including polyclonal antibodies, monoclonal antibodies including murine, human, human-adapted, humanized and chimeric monoclonal antibodies and antibody fragments.

In general, antibodies are proteins or peptide chains that exhibit binding specificity to a specific antigen. Intact antibodies are heterotetrameric glycoproteins, composed of two identical light chains and two identical heavy chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain and the light chain variable domain is aligned with the variable domain of the heavy chain. Antibody light chains of any vertebrate species can be assigned to one of two clearly distinct types, namely kappa (κ) and lambda (λ), based on the amino acid sequences of their constant domains.

Immunoglobulins can be assigned to five major classes, namely IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4.

The term "antibody fragments" means a portion of an intact antibody, generally the antigen binding or variable region of the intact antibody. Examples of antibody fragments include Fab, Fab', F(ab')$_2$ and Fv fragments, diabodies, single chain antibody molecules and multispecific antibodies formed from at least two intact antibodies.

An immunoglobulin light or heavy chain variable region consists of a "framework" region interrupted by three "antigen-binding sites". The antigen-binding sites are defined using various terms as follows: (i) Complementarity Determining Regions (CDRs) are based on sequence variability (Wu and Kabat, J. Exp. Med. 132:211-250, 1970). Generally, the antigen-binding site has six CDRs; three in the VH(H-CDR1, HCDR2, HCDR3), and three in the VL (LCDR1, LCDR2, LCDR3) (Kabat et al., Sequences of Proteins of Immunological Interest, 5th Ed. Public Health Service, National Institutes of Health, Bethesda, Md., 1991). (ii) The term "hypervariable region", "HVR", or "HV" refers to the regions of an antibody variable domain which are hypervariable in structure as defined by Chothia and Lesk (Chothia and Lesk, Mol. Biol. 196:901-917, 1987). Generally, the antigen-binding site has six hypervariable regions, three in VH(H1, H2, H3) and three in VL (L1, L2, L3). Chothia and Lesk refer to structurally conserved HVs as "canonical structures". Numbering systems as well as annotation of CDRs and HVs have recently been revised by Abhinandan and Martin (Abhinandan and Martin, Mol. Immunol. 45:3832-3239, 2008). (iii) Another definition of the regions that form the antigen-binding site has been proposed by Lefranc (Lefranc et al., Dev. Comp. Immunol. 27:55-77, 2003) based on the comparison of V domains from immunoglobulins and T-cell receptors. The International ImMunoGeneTics (IMGT) database (http:_//www_imgt_org) provides a standardized numbering and definition of these regions. The correspondence between CDRs, HVs and IMGT delineations is described in Lefranc et al., Dev. Comp. Immunol. 27:55-77, 2003. (iv) The antigen-binding site can also be delineated based on Specificity Determining Residue Usage (SDRU), according to Almagro (Almagro, Mol. Recognit. 17:132-43, 2004), where Specificity Determining Residues (SDR), refers to amino acid residues of an immunoglobulin that are directly involved in antigen contact. SDRU as defined by Almagro is a precise measure of a number and distribution of SDR for different types of antigens as defined by analyses of crystal structures of antigen-antibody complexes.

The term "consensus region" as used herein means an antigen-binding site delineated to include all amino acid residues delineated individually by Kabat, Chothia or IMGT, or any other suitable antigen-binding site delineation.

"Framework" or "framework sequence" are the remaining sequences of a variable region minus the antigen-binding sites. Because the exact definition of an antigen-binding site can be determined by various delineations as described above, the meaning of a framework sequences is subject to correspondingly different interpretations. A framework sequence as used herein means those sequences within the variable region of an antibody other than those defined to be antigen-binding site sequences.

The term "monoclonal antibody" (mAb) as used herein means an antibody (or antibody fragment) obtained from a population of substantially homogeneous antibodies. Monoclonal antibodies are highly specific, typically being directed against a single antigenic determinant. The modifier "monoclonal" indicates the substantially homogeneous character of the antibody and does not require production of the antibody by any particular method.

The term "GLP-1R biological activity" as used herein refers to any activity occurring as a result of ligand binding, for example GLP-1(7-37) to GLP-1R. Exemplary GLP-1R activities are an intracellular accumulation of cyclic AMP, calcium release, insulin secretion, or kinase-mediated phosphorylation of target proteins. Assays measuring GLP-1R biological activity are well known in the art.

The term "GLP-1R" as used herein refers to human GLP-1R protein having an amino acid sequence as shown in GenBank accession number no: NP_002053 (SEQ ID NO: 1). The mouse GLP-1R has an amino acid sequence shown in GenBank accession number no: NP_067307 (SEQ ID NO: 2).

Conventional one and three-letter amino acid codes are used herein as follows:

| Amino acid | Three-letter code | One-letter code |
|---|---|---|
| Alanine | ala | A |
| Arginine | arg | R |
| Asparagine | asn | N |
| Aspartate | asp | D |
| Cysteine | cys | C |
| Glutamate | glu | E |
| Glutamine | gln | Q |
| Glycine | gly | G |
| Histidine | his | H |
| Isoleucine | ile | I |
| Leucine | leu | L |
| Lysine | lys | K |
| Methionine | met | M |
| Phenylalanine | phe | F |
| Proline | pro | P |
| Serine | ser | S |
| Threonine | thr | T |
| Tryptophan | trp | W |
| Tyrosine | tyr | Y |
| Valine | val | V |

Compositions of Matter

The present invention relates to antibodies that are reactive with human GLP-1R, and uses of such antibodies. Such GLP-1R antibodies may have the properties of binding a GLP-1R receptor and inhibiting GLP-1R receptor-mediated signaling. Exemplary mechanisms by which GLP-1R signaling may be inhibited by such antagonists include inhibition of ligand binding, or inhibition of downstream signaling pathways. Antibodies that are reactive with human GLP-1R may also be non-neutralizing antibodies which can be used to detect GLP-1R protein in biological samples, for example serum, tissue, cells, or fixed tissue or cells. The antibodies of the invention are useful for example as research reagents, diagnostic reagents, evaluation of biodistribution of GLP-1R, and in pharmacodynamic studies. For example, GLP-1R antibodies are unlikely to cross the blood brain barrier. Thus, antagonistic GLP-1R antibodies, when dosed to animals can be used to determine the effect of selectively blocking the peripheral but not central GLP-1 activities on for example food intake. Further, antibodies specific for GLP-1R are valuable in determining the receptor levels in various sections of the brain and in the vagus nerve, as expression of GLP1-R in either could contribute to the GLP-1 effect on food intake.

One embodiment of the invention is an isolated antibody reactive with GLP-1R having the light chain complementarity determining regions (CDR) amino acid sequences (LCDR1), (LCDR2) and (LCDR3) having amino acid sequences as shown in SEQ ID NO: 3, 4 and 5, respectively, and heavy chain complementarity determining regions (CDR) amino acid sequences (HCDR1), (HCDR2) and (HCDR3) having amino acid sequences as shown in SEQ ID NO: 6, 7 and 8, respectively.

In another aspect, the invention provides an isolated antibody reactive with GLP-1R comprising a light chain variable region having the amino acid sequence shown in SEQ ID NO: 9 and a heavy chain variable region having the amino acid sequence shown in SEQ ID NO: 10.

In another aspect, the invention provides isolated light chains having the amino acid sequences shown in SEQ ID NO: 11 and 12, and isolated heavy chains having the amino acid sequences shown in SEQ ID NO: 13 and 14.

Another embodiment of the invention is an isolated antagonistic GLP-1R antibody. To generate antagonistic antibodies to the GLP-1R, the GLP-1 binding domain in the receptor must be targeted. GLP-1R belongs to a subclass of seven transmembrane G-protein coupled receptors, and it has been challenging in the past to develop antibodies against this type of receptor (Michel at al., Naunyn-Schmied Arch Pharmacol. 379:385-388, 2009; Sangawa et. al., Hybridoma 27:331-335, 2008; Huang et. al., J. Mol. Recog. 18:327-333, 2005). The GLP-1R contains a relatively large extracellular N-terminal domain that has been demonstrated to be a major determinant in GLP-1 binding affinity (Wilmen et al., Feder. Europ. Biochem. Soc. 398:43-47, 1996). Therefore, antibodies raised against the N-terminal domain are likely to compete with GLP-1R agonists for binding and consequently inhibit the downstream effects.

Exemplary antibodies may be antibodies of the IgG, IgD, IgGA or IgM isotypes. Additionally, such antibodies can be post-translationally modified by processes such as glycosylation, isomerization, deglycosylation or non-naturally occurring covalent modification such as the addition of polyethylene glycol moieties (pegylation) and lipidation. Such modifications may occur in vivo or in vitro. For example, the antibodies of the invention can be conjugated to polyethylene glycol (PEGylated) to improve their pharmacokinetic profiles. Conjugation can be carried out by techniques known to those skilled in the art. Conjugation of therapeutic antibodies with PEG has been shown to enhance pharmacodynamics while not interfering with function (Deckert et al., Int. J. Cancer 87:382-390, 2000; Knight et al., Platelets 15:409-418, 2004; Leong et al., Cytokine 16:106-119, 2001; and Yang et al., Protein Eng. 16:761-770, 2003).

Pharmacokinetic properties of the antibodies of the invention could also be enhanced through Fc modifications by techniques known to those skilled in the art. For example, IgG4 isotype heavy chains contain a Cys-Pro-Ser-Cys (CPSC) motif in the hinge region capable of forming either inter- or intra-heavy chain disulfide bonds, i.e., the two Cys residues in the CPSC motif may disulfide bond with the corresponding Cys residues in the other heavy chain (inter) or the two Cys residues within a given CPSC motif may disulfide bond with each other (intra). It is believed that in vivo isomerase enzymes are capable of converting inter-heavy chain bonds of IgG4 molecules to intra-heavy chain bonds and vice versa (Aalberse and Schuurman, Immunology 105: 9-19, 2002). Accordingly, since the heavy:light chain pairs in those IgG4 molecules with intra-heavy chain bonds in the hinge region are not covalently associated with each other, they may dissociate into HL monomers that then reassociate with HL monomers derived from other IgG4 molecules forming bispecific, heterodimeric IgG4 molecules. In a bispecific IgG antibody the two Fabs of the antibody molecule differ in the epitopes that they bind. Substituting the Ser residue in the hinge region CPSC motif of IgG4 with Pro results in "IgG1-like behavior," i.e., the molecules form stable disulfide bonds between heavy chains and therefore, are not susceptible to HL exchange with other IgG4 molecules. In one embodiment, the antibodies of the invention will comprise an IgG4 Fc domain with a S to P mutation in the CPSC motif. The location of the CPSC motif is typically found at residue 228 of a mature heavy chain but can change depending on CDR lengths.

Further, amino acid sequences can be changed or removed within the Fc domain that affect binding to Fc receptors other than an FcRn salvage receptor in the antibodies of the invention. For example, the antibody Fc regions involved in ADCC activity can be removed in the antibodies of the invention. For example, mutation of Leu234/Leu235 in the hinge region of IgG1 to L234A/L235A or Phe235/Leu236 in the hinge region of IgG4 to P235A/L236A minimizes FcR binding and reduces the ability of the immunoglobulin to mediate complement dependent cytotoxicity and ADCC. In one embodiment, the antibodies of the invention will comprise an IgG4 Fc domain with a P235A/L236A mutations. The location of these residues identified above is typical in a mature heavy chain but can change depending on CDR lengths.

The antibody antagonists of the invention may bind GLP-1R with a $K_d$ less than or equal to about $10^{-7}$, $10^{-8}$, $10^{-9}$, $10^{-10}$, $10^{-11}$ or $10^{-12}$ M. The affinity of a given molecule for a GLP-1R can be determined experimentally using any suitable method. Such methods may utilize Biacore or KinExA instrumentation, ELISA or competitive binding assays known to those skilled in the art.

Antagonist antibody molecules binding to GLP-1R with a desired affinity can be selected from libraries of variants or fragments by techniques including antibody affinity maturation. Antagonist antibodies can be identified based on their inhibition of GLP-1R biological activity using any suitable method. Such methods may utilize reporter-gene assays or assays measuring intracellular cyclic AMP production known to those skilled in the art. Suitable antibodies for distribution and pharmacodynamic studies can be tested using routine methodology, such as immunohistochemistry or ELISA assays.

Antibodies of the present invention can be produced by a variety of techniques, for example by the hybridoma method of Kohler et al., Nature 256:495-497, 1975. Chimeric mAbs containing a light chain and heavy chain variable region derived from a donor antibody (typically murine) in association with light and heavy chain constant regions derived from an acceptor antibody (typically another mammalian species such as human) can be prepared by the method disclosed in U.S. Pat. No. 4,816,567. CDR-grafted mAbs having CDRs derived from a non-human donor immunoglobulin (typically murine) and the remaining immunoglobulin-derived parts of the molecule being derived from one or more human immunoglobulins can be prepared by techniques known to those skilled in the art such as that disclosed in U.S. Pat. No. 5,225,539. Human framework sequences useful for grafting can be selected from relevant databases by those skilled in the art. Optionally, CDR-grafted mAbs can be further humanized by incorporating altered framework support residues to preserve binding affinity by techniques such as those disclosed in Queen et al., Proc. Natl. Acad. Sci. (USA), 86:10029-10032, 1989 and Hodgson et al., Bio/Technology, 9:421, 1991. Fully human mAbs lacking any non-human sequences can be prepared from human immunoglobulin transgenic mice by techniques referenced in, e.g., Lonberg et al., Nature 368:856-859, 1994; Fishwild et al., Nature Biotechnology 14:845-851, 1996; and Mendez et al., Nature Genetics 15:146-156, 1997.

Human mAbs can also be prepared and optimized from phage display libraries by techniques referenced in, e.g., Knappik et al., J. Mol. Biol. 296:57-86, 2000; and Krebs et al., J. Immunol. Meth. 254:67-84 2001.

Preparation of Immunogenic Antigens, and Monoclonal Antibody production can be performed using any suitable technique such as recombinant protein production. The immunogenic antigens can be administered to an animal in the form of purified protein, or protein mixtures including whole cells or cell or tissue extracts, or the antigen can be formed de novo in the animal's body from nucleic acids encoding said antigen or a portion thereof.

Another embodiment of the invention is an isolated polynucleotide encoding the antibodies of the invention or their complement. Exemplary polynucleotides are disclosed herein, however, other polynucleotides which, given the degeneracy of the genetic code or codon preferences in a given expression system, encode the antibody of the invention are also within the scope of the invention. Exemplary isolated polynucleotides comprise the polynucleotides having a sequence shown in SEQ ID NO: 15 or 16. The isolated nucleic acids of the present invention can be made using (a) recombinant methods, (b) synthetic techniques, (c) purification techniques, or combinations thereof, as well-known in the art. DNA encoding the monoclonal antibodies is readily isolated and sequenced using methods known in the art (e.g., by using oligonucleotide probes that are capable of binding specifically to genes encoding the heavy and light chains of murine antibodies). Where a hybridoma is produced, such cells can serve as a source of such DNA. Alternatively, using display techniques wherein the coding sequence and the translation product are linked, such as phage or ribosomal display libraries, the selection of the binder and the nucleic acid is simplified. After phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria.

Another embodiment of the invention is a vector comprising at least one polynucleotide of the invention. Such vectors may be plasmid vectors, viral vectors, transposon based vectors or any other vector suitable for introduction of the polynucleotides of the invention into a given organism or genetic background by any means. An exemplary vector for expression polypeptides of the invention consists of a CMV promoter, T7 binding site, VH leader sequence, BGH polyA site, f1 origin of replication, ColE1 origin, CMV promoter, and beta-lactamase, and may include polynucleotides encoding an antibody constant region, for example a mouse gamma2a constant region.

Another embodiment of the invention is a host cell comprising any of the polynucleotides of the invention such as a polynucleotide encoding a polypeptide comprising an immunoglobulin light chain having the amino acid sequence shown in SEQ ID NO: 11 or an immunoglobulin heavy chain having the amino acid sequence shown in SEQ ID NO: 13. Such host cells may be eukaryotic cells, bacterial cells, plant cells or archeal cells. Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, Va., CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL- TIB-196). Other useful cell lines include those derived from Chinese Hamster Ovary (CHO) cells such as CHO-K1SV (Lonza Biologics), CHO-K1 (ATCC CRL-61, Invitrogen) or DG44.

Another embodiment of the invention is a method of making an antibody reactive with GLP-1R comprising culturing a host cell of the invention and recovering the antibody produced by the host cell. Methods of making antibodies and purifying them are well known in the art.

Another embodiment of the invention is a hybridoma cell line that produces an antibody of the invention.

Example 1

Generation of Soluble GLP-1R Protein cDNAs encoding soluble human and mouse GLP-1 receptors corresponding to amino acids 24-145 of human (SEQ ID NO: 1) and amino acids 21-143 of mouse (SEQ ID NO: 2) GLP-1 receptor were prepared using gene synthesis techniques (U.S. Pat. No. 6,670,127; U.S. Pat. No. 6,521,427). Plasmids for expression of the synthetic soluble receptors were prepared using standard molecular biology techniques. Each plasmid encoded a Kozak sequence, a human growth hormone signal sequence, the soluble region of human or murine GLP-1R, and a C-terminal 6×His tag for easy purification. Vectors were transiently transfected into HEK293T cells using standard methods and the secreted proteins were purified by IMAC using Talon resin.

The soluble human GLP-1R antigen (#3527) was labeled with biotin using EZ link Sulfo-NHS-LC-biotin according to the manufacturer's instructions (Pierce Chemical Company, St. Louis, Mo.). Activity of biotinylated 3527 was confirmed using CNT0736, a GLP-1 Mimetibody™ construct (Picha et al., Diabetes 57:1926-34, 2008). A 96-well Maxisorp plate was coated (100 µl/well) with 5-µg/mL of either biotinylated or unlabeled 3527 and incubated at 4° C. overnight. Plates were washed with TBST and blocked with 300 µl/well of 1× Chemiblocker for 1 hour at RT. Plates were washed with TBST. Serial dilutions (1:3) of either CNT0736 or CNT01996 (negative control lacking the GLP-1 peptide) were made starting at 10 µg/ml, added to the appropriate wells in the plate (100 µl/well), and allowed to bind for 1 hr at RT. Plates were washed with TBST. Plates were treated for 1 hour at RT with 100 µl/well of goat anti-human IgG (H+L)-AP detection antibody diluted 1:5000 in TBST. AttoPhos substrate (1:5) detected AP activity. Biotinylated 3527 retained a comparable binding profile relative to unlabeled 3527 (data not shown).

Example 2

Identification of Anti-Human GLP-1R Antibodies

Solution panning of the Human Combinatorial Antibody Library GOLD (HuCAL GOLD) was performed using a biotinylated antigen-streptavidin magnetic bead capture method as described (Rothe et al., J. Mol. Biol. 376:1182-1200, 2008; Steidl et al., Mol. Immunol. 46: 135-144, 2008) in three subsequent rounds. Fabs recovered from the last round of selection were subcloned into the pMORPHx9_Mx_MH Fab expression vector containing a Myc and His6 tag (Rauchenberger et al., J. Biol. Chem. 278: 38194-38205, 2003). E. coli TG1 cells (#200123, Stratagene, La Jolla, Calif.) were transformed via electroporation, and the Fabs produced by the bacteria.

Fabs were screened for binding to 3527 (Rauchenberger et al., J. Biol. Chem. 278:38194-38205, 2003). Fabs that bound 3527 greater than five times background were sequenced to determine the number of unique Fab clones. 39 Fabs were selected for sequencing. From the 39 clones sequenced, PHD191 was identified 3 times, or 8% of the total hits. The amino acid sequences of the CDRs and light and heavy chain variable regions of PHD191 are shown in SEQ ID NOs: 3-10.

Example 3

Figure 1:
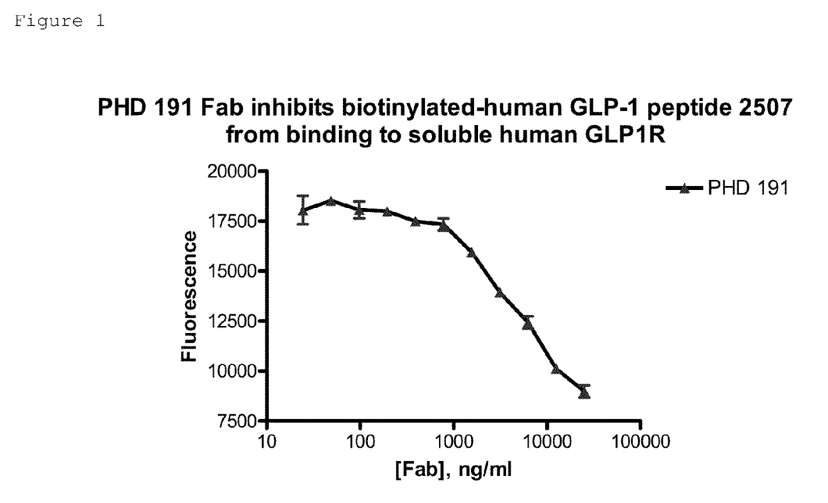
FIG. 1. PHD 191 inhibited GLP-1 peptide from binding to soluble human GLP-1R.

PHD 191 Fab Inhibits GLP-1 Binding to Soluble Human GLP-1R 96-well Maxisorp plates were coated (100 µl/well) with 5 µg/ml of soluble human GLP-1R (shGLP1-R) in PBS and incubated at 4° C. overnight. Plates were washed with TBST and blocked with 300 µl/well of 1× Chemiblocker for 1 hour at RT. Plates were washed with TBST. A mixture was made of (1:2) serial dilutions of PHD 191 Fab starting at 25 µg/ml and biotinylated human GLP-1 peptide held constant at 75 ng/ml. This mixture was added (100 µl/well) to the plates and incubated at RT for 1 hour. Plates were washed with TBST. Plates were treated for 1 hr at RT with 100 µl/well of Strep-AP detection antibody diluted 1:2000 in TBST. AttoPhos substrate (1:5) detected AP activity. PHD 191 inhibited human GLP-1 peptide binding to soluble human GLP-1R (FIG. 1).

Example 4

Transfer of PHD 191 to Human IgG1/Human IgKappa and Murine IgG2a/Murine IgKappa Formats PHD 191 was sub-cloned into full-length immunoglobulin expression vectors (Krebs et al., J. Immunol. Meth. 254:67-84, 2001). Similar constructs were created for the PHD 191 murine IgKappa, human IgG1, and human IgKappa constructs.

Full-length heavy and light chain vectors were transformed into DH10B cells according to the manufacturer's instructions. Individual colonies were screened for insertion of the correct variable region by PCR and sequence analysis. DNA was isolated for each of the correct clone and used for transfections using standard procedures, and the inserts were sequenced. The amino acid sequences of the resulting light and heavy chains are shown in SEQ ID NOs: 11-14.

The vectors encoding appropriate heavy and light chain partners were co-transfected into HEK293E cells. Supernatants containing the secreted antibodies were affinity purified using Protein A resin according to standard protocols.

Example 5

Characterization of PHD 191

Cross-Reactivity with Murine GLP-1R

The binding specificity of PHD 191 was characterized using two different ELISA assay formats. Both assay formats showed that PHD 191 binds human GLP-1R and also cross-reacts with murine GLP-1R. The first characterization assay was a neutravidin capture assay. 96-well Maxisorp plates were coated (100 µl/well) with 5 µg/ml of neutravidin in PBS and were incubated at 4° C. overnight. Coated plates were washed with TBST. 2 µg/ml of biotinylated soluble murine GLP-1R (3445), biotinylated soluble human GLP-1R (3527), or other biotinylated control proteins (mouse IL-23, mouse IL-12, mouse IL-18, rat transferrin) were added (100 μl/well) and allowed to bind to neutravidin for 1 hour at RT. Plates were washed with TBST and blocked with 300 μl/well of 1× Chemiblocker for 1 hour at RT. Plates were washed with TBST. Serial dilutions (1:2) of the PHD 191 mAb were made starting at 5 μg/ml, added to the plate (100 μl/well), and allowed to bind for 1 hr at RT. Plates were washed with TBST. Plates were treated for 1 hour at RT with 100 μl/well of goat anti-human IgG (H+L)-AP detection antibody diluted 1:5000 in TBST. AttoPhos substrate (1:5) detected AP activity. PHD 191 bound specifically to human soluble GLP-1R, cross-reacted with murine soluble GLP-1R and had no binding to unrelated biotinylated proteins (0.4 nM and 2.5 nM for human and murine soluble GLP-1R, respectively).

To confirm the cross-reactivity of PHD 191 to murine GLP-1R, a second characterization assay was performed using unlabeled receptor coated directly onto the plate. 96-well Maxisorp plates were coated (100 μl/well) with 5 μg/ml of unlabeled murine or human GLP-1R in PBS and were incubated at 4° C. overnight. Coated plates were washed with TBST and blocked with 300 μl/well of 1× Chemiblocker for 1 hour at RT. Plates were washed with TBST. Serial dilutions (1:3) of the PHD 191 Mab were made starting at 30 μg/ml, added to the plate (100 μl/well), and allowed to bind for 1 hr at RT. Plates were washed with TBST. Plates were treated for 1 hour at RT with 100 μl/well of goat anti-human IgG (H+L)-AP detection antibody diluted 1:5000 in TBST. AttoPhos substrate (1:5) detected AP activity. The direct coat assay confirmed that PHD 191 cross-reacted with soluble murine GLP-1R (0.8 nM and 11.9 nM, for human and murine soluble GLP-1R, respectively).

Inhibition of GLP-1 Binding to the Human GLP-1R

Figure 2:
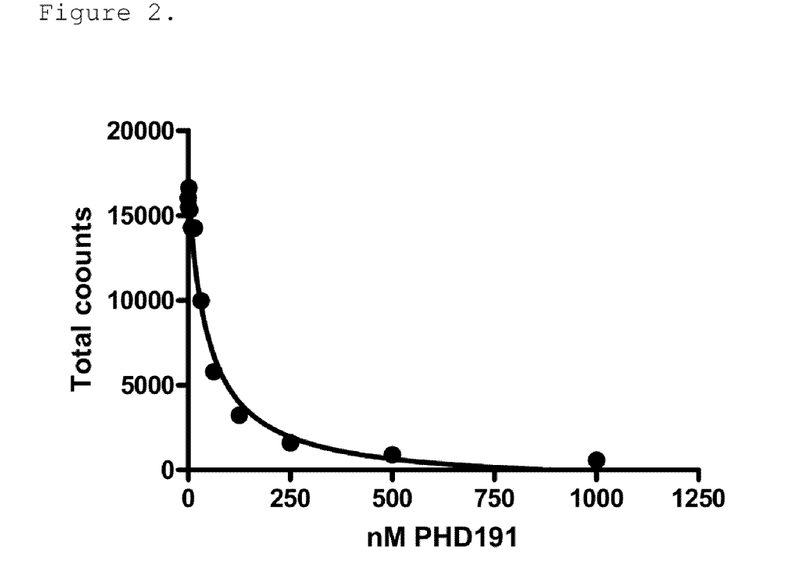
FIG. 2. PHD 191 inhibited $^{125}$I-GLP-1 binding to the human receptor.

An $^{125}$I GLP-1 binding assay was used to determine whether PHD 191 could inhibit GLP-1 peptide binding to the human receptor expressed on cells. HEK293F cells over-expressing the human GLP-1 receptor were incubated overnight at 4° C. in the presence of 3 nM $^{125}$I GLP-1 along with a dose titration of PHD 191. Unbound $^{125}$I GLP-1 was washed away and cell associated counts were measured. The data were fit to a hyperbola to obtain an $IC_{50}$ of 48.5 nM (FIG. 2). Assuming a Kd for GLP-1 binding to the human GLP-1R of 3 nM (determined previously) and competitive inhibition, this data indicates that the Ki for PHD 191 is approximately 20 nM.

Inhibition of Cyclic AMP Stimulation by GLP-1

Two assay formats were used to show that PHD 191 inhibited GLP-1 mediated cAMP accumulation. In the first format, a dose titration of PHD 191 in the presence of 0.3 nM GLP-1 peptide was added to HEK293F cells over-expressing the human GLP-1R receptor. In the second format, a dose response of GLP-1 peptide in the presence of 1 μM PHD 191 was added to the GLP-1R over-expressing cells. In both cases, total cAMP accumulation after seven minutes of stimulation was quantitated using the PerkinElmer LANCE cAMP Assay Kit. The dose titration of PHD 191 dose-dependently reduced the GLP-1 dependent cAMP accumulation, indicating a reduction in signaling of the GLP-1 peptide in the presence of the antibody. The data were fit to an equation describing a single binding event, providing an $IC_{50}$ of 3.3 nM. PHD 191 also shifted the $EC_{50}$ from 0.3 to 1.5 nM when GLP-1 peptide was tested in a cAMP assay.

Example 6

Tissue Distribution of Human GLP-1R

Protein expression of human GLP-1R was assessed in normal tissues by immunohistochemistry. GLP-1R protein was detected in pancreatic islets, CNS neurons and epithelial cells from gut.

The brain samples from normal donors were obtained from Analytical Biological Services, Inc. The brain dissections were made and qualified by a neurobiologist (Analytical Biological Services, Inc). Samples of other normal human tissues were obtained from the QualTek tissue bank, and qualified by a pathologist. Immunohistochemistry on human tissues was performed in the following manner. Four-micron tissue sections were cut from formalin fixed paraffin embedded blocks, placed on glass slides, and dried at 60° C. These were dew-axed through four 5-minute changes of xylene, followed by a graded alcohol series to distilled water. All tissue samples were tested for immunohistochemical reactivity to PHD 191 using the following protocol. Briefly, tissues were pretreated using sHIER 2 for 20 minutes and then digested for 10 minutes with Pro K at 1:15 dilution. Tissue samples were subsequently incubated with the primary antibody, PHD 191 for 63 hours at 4° C. at either 5 μg/ml or 7.5 μg/ml. For blocking experiments the tissues were incubated with PHD 191 in the presence of 20 molar excess of extracellular domain of GLP-1R. Mouse nonspecific isotype control antibody was used to confirm the specificity of staining. An ABC detection system using the MIPE protocol on the Techmate was used to label the bound primary antibody. After staining, slides were dehydrated through an alcohol series to absolute ethanol followed by xylene rinses. Slides were permanently coverslipped with glass coverslips and permount. Slides were examined under a microscope to assess staining. Positive staining is indicated by the presence of a brown chromogen (DAB-HRP) reaction product. Hematoxylin counterstain provided a blue nuclear stain to assess cell and tissue morphology. Representative images were obtained with an Olympus Microfire digital camera (M/N S97809) attached to an Olympus BX60 microscope and displayed on a Dell flat panel monitor with the DPI set at 96 and the screen resolution set at 1152 by 864 pixels. Images were brought into sharp focus using Koehler illumination. Some images taken with 40× or higher objective were taken as a series through the focal range of the field of view and combined with the Image-Pro Plus 5.1 (MediaCybernetics) extended depth of field function to obtain a composite image with sharp focus throughout the image field of view.

Pancreatic islets were identified in human pancreas section based on histological evaluation after a hematoxylin counterstain. IHC analysis of human pancreas showed the presence of human GLP-1R in islet cells. The specificity of staining was confirmed in blocking experiments where pre-incubation of PHD191 with extracellular domain of GLP-1R completely inhibited the staining. The GLP-1R was also detected in neurons in the amygdala, hypothalamus, arcuate nucleus, and area postrema. GLP-1R was not detected in two samples of brain cortex. No staining was detected in any brain sections stained with mouse nonspecific isotype control antibody.

In tissue samples containing epithelium, staining was occasionally seen in epithelial cells. In four of 14 lung samples some of the bronchial airways had epithelial cells with staining at the luminal surface and perinuclear staining in basal cells. In two of 4 colon samples, the luminal surface had strong staining. In one of 3 breast samples, perinuclear staining was seen in cells lining the ducts. No reactivity was seen in the negative controls for these samples.

In one of 3 samples of small intestine and in two of 4 colon samples, reactivity was seen in isolated crypt cells. The location and frequency of these stained crypt cells in the colon and small intestine is consistent with entero-endocrine cells.

Reactive immune cells were observed in a majority of the tissues. These were typically polymorphonuclear granulocytes within blood vessels or cells with macrophage or mast cell morphology. To confirm the specificity of staining, IHC was repeated with a subset of samples in the presence of an excess of antigen (N-terminal domain of GLP-1R). Under these conditions, PHD 191 reactivity was significantly inhibited in neurons, epithelial, and pancreatic islet cells. Only partial inhibition of PHD 191 reactivity in immune cells was observed, thus the specificity of PHD 191 staining in immune cells remains to be determined.

The data described here details the discovery and characterization of PHD 191. PHD 191 cross-reacted with murine GLP-1R and bound to human GLP-1R expressed on cells. PHD 191 was cloned into either a human IgG1 or mouse IgG2a format. PHD 191 inhibited GLP-1 binding to the human GLP-1 receptor and inhibited GLP-1 mediated cAMP accumulation. Antibodies with these properties are not available from a commercial source.

The present invention now being fully described, it will be apparent to one of ordinary skill in the art that many changes and modifications can be made thereto without departing from the spirit or scope of the appended claims.

We claim:

1. An isolated antibody reactive with glucagon-like peptide receptor 1 (GLP-1R) comprising the amino acid sequences of the light chain complementarity determining regions (CDRs) 1, 2 and 3 as shown in SEQ ID NOs: 3, 4 and 5, respectively and the amino acid sequences of the heavy chain CDRs 1, 2 and 3 as shown in SEQ ID NOs: 6, 7 and 8, respectively.

2. An isolated antibody reactive with glucagon-like peptide receptor 1 (GLP-1R) comprising a light chain variable region (VL) having the amino acid sequence shown in SEQ ID NO: 9 and a heavy chain variable region (VH) having the amino acid sequence shown in SEQ ID NO: 10.

3. An isolated antibody reactive with glucagon-like peptide receptor 1 (GLP-1R) comprising a light chain (LC) having the amino acid sequence shown in SEQ ID NO: 11 and a heavy chain (HC) having the amino acid sequence shown in SEQ ID NO: 13.

4. An isolated antibody reactive with glucagon-like peptide receptor 1 (GLP-1R) comprising a light chain (LC) having the amino acid sequence shown in SEQ ID NO: 12 and a heavy chain (HC) having the amino acid sequence shown in SEQ ID NO: 14.

5. The isolated antibody of claim 1, 2, 3 or 4 wherein the antibody is an antagonist of GLP-1R.

6. A Fab fragment of the isolated antibody of claim 1, 2, 3 or 4.

7. The isolated antibody of claim 1, 2, 3 or 4 having an isotype selected from a group consisting of human IgG1 and mouse IgG2a.

* * * * *

SEQUENCE LISTING

```
<160> NUMBER OF SEQ ID NOS: 17

<210> SEQ ID NO 1
<211> LENGTH: 463
<212> TYPE: PRT
<213> ORGANISM: Homo sapiens

<400> SEQUENCE: 1

Met Ala Gly Ala Pro Gly Pro Leu Arg Leu Ala Leu Leu Leu Leu Gly
1               5                   10                  15

Met Val Gly Arg Ala Gly Pro Arg Pro Gln Gly Ala Thr Val Ser Leu
            20                  25                  30

Trp Glu Thr Val Gln Lys Trp Arg Glu Tyr Arg Arg Gln Cys Gln Arg
        35                  40                  45

Ser Leu Thr Glu Asp Pro Pro Pro Ala Thr Asp Leu Phe Cys Asn Arg
    50                  55                  60

Thr Phe Asp Glu Tyr Ala Cys Trp Pro Asp Gly Glu Pro Gly Ser Phe
65                  70                  75                  80

Val Asn Val Ser Cys Pro Trp Tyr Leu Pro Trp Ala Ser Ser Val Pro
                85                  90                  95

Gln Gly His Val Tyr Arg Phe Cys Thr Ala Glu Gly Leu Trp Leu Gln
            100                 105                 110

Lys Asp Asn Ser Ser Leu Pro Trp Arg Asp Leu Ser Glu Cys Glu Glu
        115                 120                 125

Ser Lys Arg Gly Glu Arg Ser Ser Pro Glu Glu Gln Leu Leu Phe Leu
    130                 135                 140

Tyr Ile Ile Tyr Thr Val Gly Tyr Ala Leu Ser Phe Ser Ala Leu Val
145                 150                 155                 160

Ile Ala Ser Ala Ile Leu Leu Gly Phe Arg His Leu His Cys Thr Arg
                165                 170                 175

Asn Tyr Ile His Leu Asn Leu Phe Ala Ser Phe Ile Leu Arg Ala Leu
            180                 185                 190

Ser Val Phe Ile Lys Asp Ala Ala Leu Lys Trp Met Tyr Ser Thr Ala
        195                 200                 205

Ala Gln Gln His Gln Trp Asp Gly Leu Leu Ser Tyr Gln Asp Ser Leu
    210                 215                 220

Ser Cys Arg Leu Val Phe Leu Leu Met Gln Tyr Cys Val Ala Ala Asn
225                 230                 235                 240

Tyr Tyr Trp Leu Leu Val Glu Gly Val Tyr Leu Tyr Thr Leu Leu Ala
                245                 250                 255

Phe Ser Val Leu Ser Glu Gln Trp Ile Phe Arg Leu Tyr Val Ser Ile
            260                 265                 270

Gly Trp Gly Val Pro Leu Leu Phe Val Val Pro Trp Gly Ile Val Lys
        275                 280                 285

Tyr Leu Tyr Glu Asp Glu Gly Cys Trp Thr Arg Asn Ser Asn Met Asn
```

```
                290                 295                 300
Tyr Trp Leu Ile Ile Arg Leu Pro Ile Leu Phe Ala Ile Gly Val Asn
305                 310                 315                 320

Phe Leu Ile Phe Val Arg Val Ile Cys Ile Val Val Ser Lys Leu Lys
                325                 330                 335

Ala Asn Leu Met Cys Lys Thr Asp Ile Lys Cys Arg Leu Ala Lys Ser
                340                 345                 350

Thr Leu Thr Leu Ile Pro Leu Leu Gly Thr His Glu Val Ile Phe Ala
                355                 360                 365

Phe Val Met Asp Glu His Ala Arg Gly Thr Leu Arg Phe Ile Lys Leu
                370                 375                 380

Phe Thr Glu Leu Ser Phe Thr Ser Phe Gln Gly Leu Met Val Ala Ile
385                 390                 395                 400

Leu Tyr Cys Phe Val Asn Asn Glu Val Gln Leu Glu Phe Arg Lys Ser
                405                 410                 415

Trp Glu Arg Trp Arg Leu Glu His Leu His Ile Gln Arg Asp Ser Ser
                420                 425                 430

Met Lys Pro Leu Lys Cys Pro Thr Ser Ser Leu Ser Ser Gly Ala Thr
                435                 440                 445

Ala Gly Ser Ser Met Tyr Thr Ala Thr Cys Gln Ala Ser Cys Ser
                450                 455                 460

<210> SEQ ID NO 2
<211> LENGTH: 463
<212> TYPE: PRT
<213> ORGANISM: Mus musculus

<400> SEQUENCE: 2

Met Ala Ser Thr Pro Ser Leu Leu Arg Leu Ala Leu Leu Leu Leu Gly
 1               5                  10                  15

Ala Val Gly Arg Ala Gly Pro Arg Pro Gln Gly Thr Thr Val Ser Leu
                20                  25                  30

Ser Glu Thr Val Gln Lys Trp Arg Glu Tyr Arg Arg Gln Cys Gln Arg
                35                  40                  45

Phe Leu Thr Glu Ala Pro Leu Leu Ala Thr Gly Leu Phe Cys Asn Arg
50                  55                  60

Thr Phe Asp Asp Tyr Ala Cys Trp Pro Asp Gly Pro Pro Gly Ser Phe
65                  70                  75                  80

Val Asn Val Ser Cys Pro Trp Tyr Leu Pro Trp Ala Ser Ser Val Leu
                85                  90                  95

Gln Gly His Val Tyr Arg Phe Cys Thr Ala Glu Gly Leu Trp Leu His
                100                 105                 110

Lys Asp Asn Ser Ser Leu Pro Trp Arg Asp Leu Ser Glu Cys Glu Glu
                115                 120                 125

Ser Lys Arg Gly Glu Arg Asn Phe Pro Glu Glu Gln Leu Leu Ser Leu
                130                 135                 140

Tyr Ile Ile Tyr Thr Val Gly Tyr Ala Leu Ser Phe Ser Ala Leu Val
145                 150                 155                 160

Ile Ala Ser Ala Ile Leu Val Gly Phe Arg His Leu His Cys Thr Arg
                165                 170                 175

Asn Tyr Ile His Leu Asn Leu Phe Ala Ser Phe Ile Leu Arg Ala Leu
                180                 185                 190

Ser Val Phe Ile Lys Asp Ala Ala Leu Lys Trp Met Tyr Ser Thr Ala
                195                 200                 205

Ala Gln Gln His Gln Trp Asp Gly Leu Leu Ser Tyr Gln Asp Ser Leu
```

```
                    210                 215                 220
Gly Cys Arg Leu Val Phe Leu Leu Met Gln Tyr Cys Val Ala Ala Asn
225                 230                 235                 240

Tyr Tyr Trp Leu Leu Val Glu Gly Val Tyr Leu Tyr Thr Leu Leu Ala
                    245                 250                 255

Phe Ser Val Phe Ser Glu Gln Arg Ile Phe Lys Leu Tyr Leu Ser Ile
                    260                 265                 270

Gly Trp Gly Val Pro Leu Leu Phe Val Ile Pro Trp Gly Ile Val Lys
                    275                 280                 285

Tyr Leu Tyr Glu Asp Glu Gly Cys Trp Thr Arg Asn Ser Asn Met Asn
290                 295                 300

Tyr Trp Leu Ile Ile Arg Leu Pro Ile Leu Phe Ala Ile Gly Val Asn
305                 310                 315                 320

Phe Leu Ile Phe Ile Arg Val Ile Cys Ile Val Ser Lys Leu Lys
                    325                 330                 335

Ala Asn Leu Met Cys Lys Thr Asp Ile Lys Cys Arg Leu Ala Lys Ser
                340                 345                 350

Thr Leu Thr Leu Ile Pro Leu Leu Gly Thr His Glu Val Ile Phe Ala
                    355                 360                 365

Phe Val Met Asp Glu His Ala Arg Gly Thr Leu Arg Phe Ile Lys Leu
                    370                 375                 380

Phe Thr Glu Leu Ser Phe Thr Ser Phe Gln Gly Leu Met Val Ala Ile
385                 390                 395                 400

Leu Tyr Cys Phe Val Asn Asn Glu Val Gln Met Glu Phe Arg Lys Cys
                    405                 410                 415

Trp Glu Arg Trp Arg Leu Glu His Leu Asn Ile Gln Arg Asp Cys Ser
                    420                 425                 430

Met Lys Pro Leu Lys Cys Pro Thr Ser Val Ser Ser Gly Ala Thr
                435                 440                 445

Val Gly Ser Ser Val Tyr Ala Ala Thr Cys Gln Ser Ser Tyr Ser
    450                 455                 460

<210> SEQ ID NO 3
<211> LENGTH: 12
<212> TYPE: PRT
<213> ORGANISM: Artificial Sequence
<220> FEATURE:
<223> OTHER INFORMATION: Light Chain CDR1

<400> SEQUENCE: 3

Arg Ala Ser Gln Tyr Gly Ser Ser Ser Tyr Leu Ala
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Light Chain CDR2

<400> SEQUENCE: 4

Asp Ala Ser Asn Arg Ala Thr
1               5

<210> SEQ ID NO 5
<211> LENGTH: 9
<212> TYPE: PRT
<213> ORGANISM: Artificial Sequence
<220> FEATURE:
<223> OTHER INFORMATION: Light Chain CDR3
```

```
<400> SEQUENCE: 5

Gln Gln Tyr Ser Asp Trp Pro Phe Thr
 1               5

<210> SEQ ID NO 6
<211> LENGTH: 3
<212> TYPE: PRT
<213> ORGANISM: Artificial Sequence
<220> FEATURE:
<223> OTHER INFORMATION: Heavy Chain CDR1

<400> SEQUENCE: 6

Ala Ile His
 1

<210> SEQ ID NO 7
<211> LENGTH: 17
<212> TYPE: PRT
<213> ORGANISM: Artificial Sequence
<220> FEATURE:
<223> OTHER INFORMATION: Heavy Chain CDR2

<400> SEQUENCE: 7

Gly Ile Ile Pro Ile Phe Gly Met Ala Asp Tyr Ala Gln Lys Phe Gln
 1               5                  10                  15

Gly

<210> SEQ ID NO 8
<211> LENGTH: 10
<212> TYPE: PRT
<213> ORGANISM: Artificial Sequence
<220> FEATURE:
<223> OTHER INFORMATION: Heavy Chain CDR3

<400> SEQUENCE: 8

Thr Asp Tyr Gly Phe Arg Ala Leu Asp Tyr
 1               5                  10

<210> SEQ ID NO 9
<211> LENGTH: 110
<212> TYPE: PRT
<213> ORGANISM: Artificial Sequence
<220> FEATURE:
<223> OTHER INFORMATION: Light chain variable region

<400> SEQUENCE: 9

Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Tyr Gly Ser Ser Ser
                20                  25                  30

Tyr Leu Ala Trp Tyr Gln Gln Lys Pro Gly Gln Ala Pro Arg Leu Leu
         35                  40                  45

Ile Tyr Asp Ala Ser Asn Arg Ala Thr Gly Val Pro Ala Arg Phe Ser
     50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Tyr Ser Asp Trp Pro
                 85                  90                  95

Phe Thr Phe Gly Gln Gly Thr Lys Val Glu Ile Lys Arg Thr
            100                 105                 110

<210> SEQ ID NO 10
```

<211> LENGTH: 117
<212> TYPE: PRT
<213> ORGANISM: Artificial Sequence
<220> FEATURE:
<223> OTHER INFORMATION: Heavy chain variable region

<400> SEQUENCE: 10

```
Gln Val Glu Leu Val Gln Ser Gly Ala Glu Val Lys Pro Gly Ser
  1               5                  10                  15

Ser Val Lys Val Ser Cys Lys Ala Ser Gly Gly Thr Phe Ser Ala Ile
                 20                  25                  30

His Trp Val Arg Gln Ala Pro Gly Gln Gly Leu Glu Trp Met Gly Gly
             35                  40                  45

Ile Ile Pro Ile Phe Gly Met Ala Asp Tyr Ala Gln Lys Phe Gln Gly
         50                  55                  60

Arg Val Thr Ile Thr Ala Asp Glu Ser Thr Ser Thr Ala Tyr Met Glu
 65                  70                  75                  80

Leu Ser Ser Leu Arg Ser Glu Asp Thr Ala Val Tyr Tyr Cys Ala Arg
                 85                  90                  95

Thr Asp Tyr Gly Phe Arg Ala Leu Asp Tyr Trp Gly Gln Gly Thr Leu
            100                 105                 110

Val Thr Val Ser Ser
            115
```

<210> SEQ ID NO 11
<211> LENGTH: 215
<212> TYPE: PRT
<213> ORGANISM: Artificial Sequence
<220> FEATURE:
<223> OTHER INFORMATION: Light chain complete human kappa

<400> SEQUENCE: 11

```
Asp Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Tyr Gly Ser Ser Ser
                 20                  25                  30

Tyr Leu Ala Trp Tyr Gln Gln Lys Pro Gly Gln Ala Pro Arg Leu Leu
             35                  40                  45

Ile Tyr Asp Ala Ser Asn Arg Ala Thr Gly Val Pro Ala Arg Phe Ser
         50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Tyr Ser Asp Trp Pro
                 85                  90                  95

Phe Thr Phe Gly Gln Gly Thr Lys Val Glu Ile Lys Arg Thr Val Ala
            100                 105                 110

Ala Pro Ser Val Phe Ile Phe Pro Pro Ser Asn Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Tyr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205
```

```
Ser Phe Asp Arg Gly Glu Cys
    210             215

<210> SEQ ID NO 12
<211> LENGTH: 217
<212> TYPE: PRT
<213> ORGANISM: Artificial Sequence
<220> FEATURE:
<223> OTHER INFORMATION: Light chain complete mouse kappa

<400> SEQUENCE: 12

Asp Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Tyr Gly Ser Ser Ser
             20                  25                  30

Tyr Leu Ala Trp Tyr Gln Gln Lys Pro Gly Gln Ala Pro Arg Leu Leu
         35                  40                  45

Ile Tyr Asp Ala Ser Asn Arg Ala Thr Gly Val Pro Ala Arg Phe Ser
 50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Tyr Ser Asp Trp Pro
             85                  90                  95

Phe Thr Phe Gly Gln Gly Thr Lys Val Glu Ile Lys Arg Thr Arg Ala
            100                 105                 110

Asp Ala Ala Pro Thr Val Ser Ile Phe Pro Pro Ser Ser Glu Gln Leu
            115                 120                 125

Thr Ser Gly Gly Ala Ser Val Val Cys Phe Leu Asn Asn Phe Tyr Pro
        130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
            165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210             215

<210> SEQ ID NO 13
<211> LENGTH: 444
<212> TYPE: PRT
<213> ORGANISM: Artificial Sequence
<220> FEATURE:
<223> OTHER INFORMATION: Heavy chain complete human IgG1

<400> SEQUENCE: 13

Gln Val Glu Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ala Ile
             20                  25                  30

His Trp Val Arg Gln Ala Pro Gly Gln Gly Leu Glu Trp Met Gly Gly
         35                  40                  45

Ile Ile Pro Ile Phe Gly Met Ala Asp Tyr Ala Gln Lys Phe Gln Gly
 50                  55                  60

Arg Val Thr Ile Thr Ala Asp Glu Ser Thr Ser Thr Ala Tyr Met Glu
 65                  70                  75                  80
```

```
Leu Ser Ser Leu Arg Ser Glu Asp Thr Ala Val Tyr Tyr Cys Ala Arg
            85                  90                  95

Thr Asp Tyr Gly Phe Arg Ala Leu Asp Tyr Trp Gly Gln Gly Thr Leu
           100                 105                 110

Val Thr Val Ser Ser Ala Ser Thr Lys Gly Pro Ser Val Phe Pro Leu
           115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Ser Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 14
<211> LENGTH: 447
<212> TYPE: PRT
<213> ORGANISM: Artificial Sequence
<220> FEATURE:
<223> OTHER INFORMATION: Heavy chain complete mouse IgG2a

<400> SEQUENCE: 14
```

```
Gln Val Glu Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ala Ile
             20                  25                  30

His Trp Val Arg Gln Ala Pro Gly Gln Gly Leu Glu Trp Met Gly Gly
         35                  40                  45

Ile Ile Pro Ile Phe Gly Met Ala Asp Tyr Ala Gln Lys Phe Gln Gly
 50                  55                  60

Arg Val Thr Ile Thr Ala Asp Glu Ser Thr Ser Thr Ala Tyr Met Glu
 65                  70                  75                  80

Leu Ser Ser Leu Arg Ser Glu Asp Thr Ala Val Tyr Tyr Cys Ala Arg
                 85                  90                  95

Thr Asp Tyr Gly Phe Arg Ala Leu Asp Tyr Trp Gly Gln Gly Thr Leu
            100                 105                 110

Val Thr Val Ser Ser Ala Lys Thr Thr Ala Pro Ser Val Tyr Pro Leu
            115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
            195                 200                 205

Lys Val Asp Lys Lys Ile Glu Pro Arg Gly Pro Thr Ile Lys Pro Cys
    210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Asp Val Ser Glu Asp Asp Pro Asp
            260                 265                 270

Val Gln Ile Ser Trp Phe Val Asn Asn Val Glu Val His Thr Ala Gln
    275                 280                 285

Thr Gln Thr His Arg Glu Asp Tyr Asn Ser Thr Leu Arg Val Val Ser
290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
    370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430
```

His Asn His His Thr Thr Lys Ser Phe Ser Arg Thr Pro Gly Lys
    435                 440                 445

<210> SEQ ID NO 15
<211> LENGTH: 654
<212> TYPE: DNA
<213> ORGANISM: Artificial Sequence
<220> FEATURE:
<223> OTHER INFORMATION: Light chain complete human kappa

<400> SEQUENCE: 15

```
gatatcgtgc tgacccagag cccggcgacc ctgagcctgt ctccgggcga acgtgcgacc      60
ctgagctgca gagcgagcca gtatggttct tcttcttatc tggcttggta ccagcagaaa     120
ccaggtcaag caccgcgtct attaatttat gatgcttcta atcgtgcaac tggggtcccg     180
gcgcgtttta gcggctctgg atccggcacg gattttaccc tgaccattag cagcctggaa     240
cctgaagact ttgcggttta ttattgccag cagtattctg attggccttt tacctttggc     300
cagggtacga agttgaaat taaacgtacg cgtacggtgg ctgcaccatc tgtcttcatc      360
ttcccgccat ctgatgagca gttgaaatct ggaactgcct ctgttgtgtg cctgctgaat     420
aacttctatc ccagagaggc caaagtacag tggaaggtgg ataacgccct ccaatcgggt     480
aactcccagg agagtgtcac agagcaggac agcaaggaca gcacctacag cctcagcagc     540
accctgacgc tgagcaaagc agactacgag aaacacaaag tctacgcctg cgaagtcacc     600
catcagggcc tgagctcgcc cgtcacaaag agcttcaaca ggggagagtg ttag           654
```

<210> SEQ ID NO 16
<211> LENGTH: 1344
<212> TYPE: DNA
<213> ORGANISM: Artificial Sequence
<220> FEATURE:
<223> OTHER INFORMATION: Heavy chain complete human IgG1

<400> SEQUENCE: 16

```
caggtggaat tggttcagtc tggcgcggaa gtgaaaaaac cgggcagcag cgtgaaagtg      60
agctgcaaag cctccggagg cactttttct gctattcatt gggtgcgcca agcccctggg     120
cagggtctcg agtggatggg cggtatcatt ccgattttg gcatggcgga ttacgcgcag     180
aagtttcagg gccgggtgac cattaccgcg gatgaaagca ccagcaccgc gtatatggaa     240
ctgagcagcc tgcgtagcga agatacggcc gtgtattatt gcgcgcgtac tgattatggt     300
tttcgtgctc ttgattattg gggccaaggc accctggtga cggttagctc agcctccacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660
gacaaaactc acacatgccc accgtgccca gcacctgaac tcctgggggg accgtcagtc     720
ttcctcttcc cccaaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgggtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
```

```
                                                -continued
gggcagcccc gagaaccaca ggtgtacacc ctgcccccat cccgggatga gctgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca gagcaggtg gcagcagggg    1260 aacgtcttct catgctccgt gatgcatgag gctctgcaca accactacac gcagaagagc   1320
ctctccctgt ctccgggtaa atga                                          1344

<210> SEQ ID NO 17
<211> LENGTH: 31
<212> TYPE: PRT
<213> ORGANISM: Homo sapiens

<400> SEQUENCE: 17

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
            20                  25                  30
```